(12) United States Patent
Vilsmeier

(10) Patent No.: US 9,061,142 B2
(45) Date of Patent: Jun. 23, 2015

(54) METHOD AND DEVICE FOR RADIATION THERAPY TREATMENT OF MULTIPLE TARGETS

(75) Inventor: Stefan Vilsmeier, Munich (DE)

(73) Assignee: Brainlab AG, Feldkirchen (DE)

( * ) Notice: Subject to any disclaimer, the term of this patent is extended or adjusted under 35 U.S.C. 154(b) by 0 days.

(21) Appl. No.: 14/359,324

(22) PCT Filed: Nov. 23, 2011

(86) PCT No.: PCT/EP2011/070829
§ 371 (c)(1),
(2), (4) Date: May 20, 2014

(87) PCT Pub. No.: WO2013/075743
PCT Pub. Date: May 30, 2013

(65) Prior Publication Data
US 2014/0330065 A1  Nov. 6, 2014

(51) Int. Cl.
*A61N 5/10* (2006.01)
*G21K 5/00* (2006.01)
*G06F 19/00* (2011.01)
*G21K 5/04* (2006.01)

(52) U.S. Cl.
CPC *A61N 5/103* (2013.01); *G21K 5/00* (2013.01); *G06F 19/3481* (2013.01); *G21K 5/04* (2013.01); *A61N 5/1045* (2013.01); *A61N 5/1036* (2013.01); *A61N 5/1077* (2013.01); *A61N 2005/1087* (2013.01)

(58) Field of Classification Search
CPC ........... A61N 2005/1087; A61N 5/103; A61N 5/1036; A61N 5/1045; A61N 5/1077; G06F 19/3481; G21K 5/04; G21K 5/00
See application file for complete search history.

(56) References Cited

U.S. PATENT DOCUMENTS

| | | | |
|---|---|---|---|
| 7,741,624 B1 * | 6/2010 | Sahadevan | 250/494.1 |
| 7,835,492 B1 | 11/2010 | Sahadevan | |
| 8,139,714 B1 * | 3/2012 | Sahadevan | 378/65 |
| 8,173,983 B1 * | 5/2012 | Sahadevan | 250/494.1 |
| 8,915,833 B1 * | 12/2014 | Sahadevan | 600/1 |
| 2005/0200624 A1 * | 9/2005 | Lachner et al. | 345/427 |
| 2006/0245537 A1 * | 11/2006 | Bakai et al. | 378/9 |
| 2007/0201614 A1 * | 8/2007 | Goldman et al. | 378/65 |
| 2009/0161826 A1 * | 6/2009 | Gertner et al. | 378/65 |
| 2009/0287036 A1 * | 11/2009 | Shapiro et al. | 600/12 |
| 2010/0081971 A1 * | 4/2010 | Allison | 601/2 |

(Continued)

OTHER PUBLICATIONS

International Search Report and Written Opinion for International Application No. PCT/EP2011/070829 dated Sep. 13, 2012.

(Continued)

*Primary Examiner* — Michael Logie
(74) *Attorney, Agent, or Firm* — Tucker Ellis LLP

(57) ABSTRACT

The present invention is directed to a data processing method for determining a treatment plan for radiation therapy treatment of at least two spatially separate targets by means of a treatment device constituted to treat the at least two targets by means of one or more sub-beams during a treatment time, the one or more sub-beams constituting at least one treatment beam which is to pass through the at least two targets in accordance with a treatment plan during the treatment time, the treatment device being further constituted to allow for simultaneous treatment of the at least two targets by at least two of the sub-beams at least during a time interval during the treatment time.

15 Claims, 4 Drawing Sheets

(56) References Cited

U.S. PATENT DOCUMENTS

Figure 1:
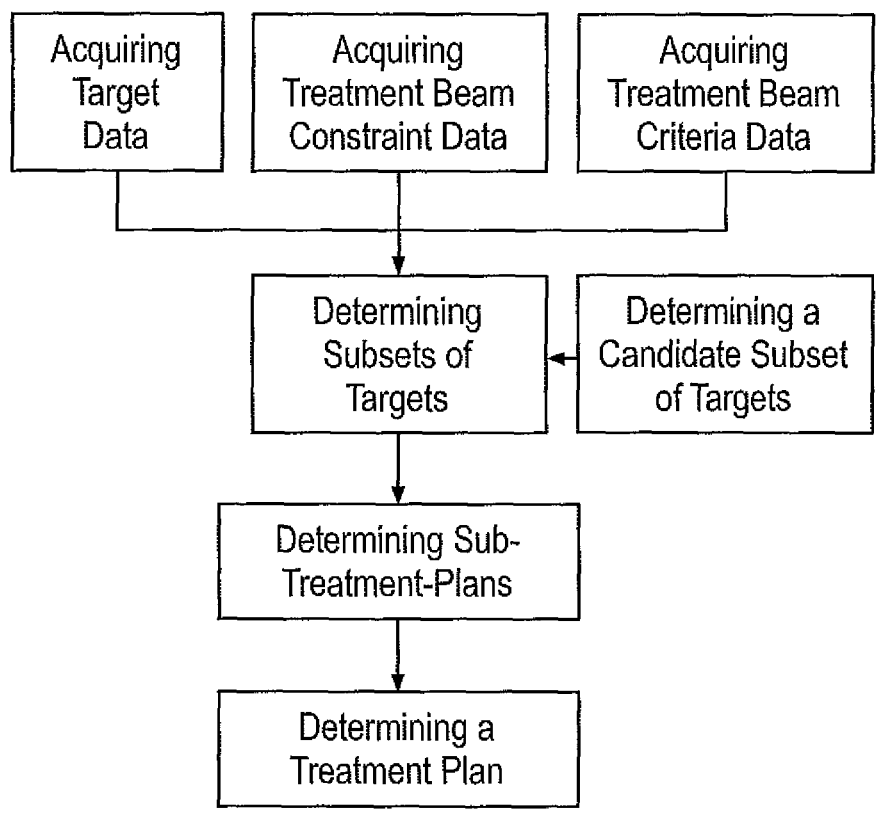

| | | | |
|---|---|---|---|
| 2010/0331833 A1* | 12/2010 | Maschke et al. | 606/20 |
| 2011/0049384 A1* | 3/2011 | Yared et al. | 250/458.1 |
| 2011/0130615 A1* | 6/2011 | Mishelevich | 600/9 |
| 2011/0222660 A1* | 9/2011 | Wang et al. | 378/65 |
| 2013/0085314 A1* | 4/2013 | Vilsmeier | 600/1 |
| 2013/0085735 A1* | 4/2013 | Vilsmeier | 703/11 |
| 2013/0222415 A1* | 8/2013 | Vilsmeier | 345/619 |
| 2013/0240623 A1* | 9/2013 | Baym et al. | 235/380 |
| 2014/0066755 A1* | 3/2014 | Matteo et al. | 600/427 |
| 2014/0171726 A1* | 6/2014 | Gum et al. | 600/1 |

OTHER PUBLICATIONS

Teh et al., "Intensity modulated radiation therapy: a new promising technology in radiation oncology", The Oncologist, vol. 4, No. 6, 1999, pp. 433-442.

Kang et al., "A method for optimizing LINAC treatment geometry for volumetric modulated arc therapy of multiple brain metastases", Medical Physics. vol. 37, No. 8, Aug. 2010, pp. 4146-4154.

\* cited by examiner

METHOD AND DEVICE FOR RADIATION THERAPY TREATMENT OF MULTIPLE TARGETS

RELATED APPLICATION DATA

This application is a national phase application of International Application No. PCT/EP2011/070829 filed Nov. 23, 2011 and published in the English language.

The present invention is directed to a data processing method of planning radiation therapy treatment of at least two targets, particularly by means of a treatment beam source and a treatment beam shaping device which directs a treatment beam to at least two targets in or on a patients body. The present invention is directed to the medical field and in particular to the determination of a treatment plan for radiotherapy treatment of patients by means of the data processing method. The present invention is in particular directed to the field of radiotherapy.

The object of the present invention is to provide a method for a radiation therapy treatment of at least two targets, wherein at least two targets are treated by means of a treatment beam.

The problem of the prior art is solved by the subject-matter of any independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment would has the same or similar function of an other feature of an other embodiment can be exchanged in particular, a feature of one embodiment which supplements a further function to another embodiment can be added to the other embodiment.

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term of computer encompasses a cloud computer, in particular a cloud server. The term of cloud computer encompasses cloud computer system in particular comprises a system of at least one cloud computer, in particular plural operatively interconnected cloud computers such as a server farm. Preferably, the cloud computer is connected to a wide area network such as the world wide web (WWW). Such a cloud computer is located in a so-called cloud of computers which are all connected to the world wide web. Such an infrastructure is used for cloud computing which describes computation, software, data access and storage services that do not require end-user knowledge of physical location and configuration of the computer that delivers a specific service. In particular, the term "cloud" is used as a metaphor for the internet (world wide web). In particular, the cloud provides computing infrastructure as a service (IaaS). The cloud computer may function as a virtual host for an operating system and/or data processing application which is used for executing the inventive method. Preferably, the cloud computer is an elastic compute cloud (EC2) provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

Preferably, the inventive method is at least partly executed by a computer. That is, all steps or just some of the steps (i.e. less than a total number of steps) of the inventive method may be executed by a computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe.

The present invention also relates to the field of controlling a treatment beam. The treatment beam treats body parts which are to be treated, which are referred to in the following as "treatment body parts". These body parts are in particular parts of a patient's body, i.e. anatomical body parts. Preferably control data are determined in accordance with the inventive date processing method which describes the control of a treatment beam by the inventive radiation therapy system in accordance with the determined treatment plan.

The present invention relates to the field of medicine and in particular to the use of beams, in particular radiation beams, to treat parts of a patient's body, which are also called treatment beams. A treatment beam treats body parts which are to be treated by means of treatment radiation, which are referred to in the following as "treatment body parts. The treatment radiation is radiation which interacts with the body parts for treatment. These body parts are in particular parts of a patient's body, i.e. anatomical body parts. Ionising radiation is in particular used as treatment radiation for the purpose of treatment. In particular, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation are X-rays, high-energy particles (high-energy particle beams) and/or ionizing radiation emitted from a radioactive element. The treatment radiation, in particular the treatment beam, is in particular used in radiation therapy, in particular radiotherapy, in particular in the field of oncology. For treating cancer in particular, parts of the body comprising a pathologic structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part. Herein, the treatment body part comprises, in particular consists of at least two spatially separate targets.

With respect to background A, reference is made to the following two web pages: http://www.elekta.com/healthcare_us_elekta_vmat.php and http://www.varian.com/us/oncology/treatments/treatment_techniques/rapidarc.

A treatment body part can be treated by one or more treatment beams issued from one or more directions at one or more times. Thus the treatment by means of the at least one treatment beam follows a spatial pattern and a time pattern which is described by a treatment plan. To describe the spatial and/or time features of the treatment by means of the at least one treatment beam, the term "beam arrangement" (also referred to as "treatment beam arrangement") is used. Thus, the treatment plan is preferably described by the treatment beam arrangement. The treatment beam arrangement is an arrangement of at least one treatment beam. The relative position of the treatment beam arrangement is preferably described relative to a reference system, in particular relative to the treatment device, the treatment room and preferably relative to the patient's body, in particular relative to the at least two targets. Preferably, the at least two targets are at rest in the reference system in which the position of the treatment beam arrangement is described. The treatment beam arrangement preferably also describes this relative position. The actual treatment of the at least two targets is preferably performed in accordance with the treatment beam arrangement determined in accordance with the invention. Thus, the term "treatment plan" preferably corresponds to the term "treatment beam arrangement".

The treatment beam arrangement describes in particular the spatial features which the at least one treatment beam shall adopt during treatment and in particular change the spatial features which shall be adopted during treatment. The spatial features comprise in particular the positions adopted by the at least one treatment beam and/or the geometry (size and/or shape) of the at least one treatment beam, in particular the position and/or geometry of sub-beams which are comprised by and in particular constitute the at least one treatment beam.

The beam positions describe the positions of the treatment beams of the beam arrangement. The arrangement of beam positions is called positional arrangement. A beam position is preferably defined by the beam direction and additional information which allows to assign a specific location in particular a three-dimensional space to the treatment beam, for example information about the coordinates in a defined coordinate system. The specific location is one point on preferably a straight line. This line is called "beam line" and runs in the beam direction and for instance runs along the central axis of the treatment beam. The defined coordinate system is preferably defined relative to the treatment device or relative to at least part of the patient's body, in particular relative to the at least two targets. The positional arrangement comprises (in particular consists of) at least one beam position, in particular a plurality of beam positions, the plurality of beam positions can comprise a discrete set of beam positions (e.g. two or more different beam positions) or a continuous multiplicity (manifold) of beam positions.

During treatment, one or more treatment beams in particular adopt the treatment beam positions defined by the positional arrangement simultaneously or sequentially (the latter in particular in case there is just one beam source to emit a treatment beam). If there are several beam sources, at least a sub-set of all beam positions can also be adopted simultaneously by treatment beams during the treatment. In particular one or more sub-sets of the treatment beams can adopt the beam positions of the arrangement in accordance with a predefined sequence. A sub set of treatment beams comprises one or more treatment beams. The full set of treatment beams which comprise one or more treatment beams and which adopts all beam positions defined by the positional arrangement is the beam arrangement.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit—CPU) which executes the computer program elements and optionally a volatile memory (in particular, a random access memory—RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The present invention is also directed to a radiotherapy system as mentioned in the claims.

Dose criteria data can describe a required coverage of respective ones of the at least two targets by the treatment beam and/or by a minimum dose level. Moreover, dose criteria data can describe a required homogeneity for the dose distribution in parts outside the targets. Dose criteria data can describe a minimum dose limit for each of the targets. Dose criteria data can describe a maximum dose limit for the parts outside the targets, in particular for critical body parts (in particular the function of which is important and not to be affected by radiation, like the visual center in the brain).

As mentioned above, the present invention in particular relates to radiotherapy, in particular to a data processing method by means of which a radiation therapy can be planned. Such a radiotherapy treatment plan in particular describes an arrangement of treatment beams. The treatment beam and the arrangement of treatment beams has been described above. The radiotherapy is used for radiotherapy of targets. The targets represent the body part which is to be treated by the treatment radiation. Herein, this body part is referred to as "treatment body part". The treatment body part is in particular a plurality of lesions or an arrangement of lesions, in particular a tumor or an arrangement of tumors, particular lesions/tumors of which already a part has been resected by surgical treatment.

According to the present invention, a data processing method is provided which is preferably used to determine a treatment plan for radiation therapy treatment of targets. Those targets are in particular spatially separate targets. The treatment is preferably performed by a treatment device. The treatment device is preferably constituted to treat the targets (which are in particular two or more targets, in particular three or more targets, in particular four or more targets), in particular simultaneously. The treatment is performed by means of at least one treatment beam which is issued by the treatment device during a treatment time (which corresponds in particular to the time of a radiotherapy treatment session). In more detail, the targets are preferably treated by one or more sub beams which are comprised by the at least one treatment beam. In particular, respective ones of the sub-beams are assigned to treat respective ones of the targets. The treatment is performed in accordance with the above-mentioned treatment plan (treatment beam arrangement). Preferably, one of the sub beams is dedicated to treat one of the targets in accordance with the treatment plan. Preferably, the treatment device is constituted to issue at least two of the sub beams simultaneously in order to allow for a simultaneous treatment at least for a time interval during the treatment time so that the treatment time can be shortened. In particular, the treatment device is constituted to allow for simultaneous treatment of at least two of the at least two targets by at least two of the sub beams at least during a time interval during treatment time. The treatment device is in particular constituted to issue spatially separate sub-beams for simultaneous treatment of the targets. In particular, the determination of the treatment plan can comprise the determination of a set of the at least two targets. The set can comprise all or less than all of the treatment targets and the number of targets within the set can change during the treatment time as described in more detail below. The determined treatment plan in particular describes the treatment of the set of targets (see below).

The determination of the treatment plan is preferably based on target data, treatment beam constraint data and treatment beam criteria data which will be described below. In particular, the treatment plan is determined to fulfil the constraints described by the treatment beam constraint data and the criteria described by the treatment beam criteria data. As far as herein the geometry (size and/or shape) of a sub beam is described, in particular the geometry of a cross-sectional area, this refers in particular to the shape, the sub beam has within the patient's body (in particular after passing through a beam shaping device).

The above-mentioned target data describe spatial information on the at least two targets which are in particular spatially separate within the patient's body. The spatial information describe in particular the geometries (size and/or shape) of the targets and/or the positions of the targets.

The target data provides in particular the spatial information about volume in space which has to absorb radiation so as to treat targets. The positions of the targets are preferably described in a reference system in which potential treatment beam arrangements (i.e. treatment beam arrangements which can be realized by the treatment device) are at rest, in particular the position is described relative to the treatment device. The positions of the targets can also be described in other reference systems. For instance, the positions of the targets can be described in a reference system in which the targets are at rest. In that case, the treatment plan (treatment beam arrangement) is preferably described in a reference system in which the targets are at rest. Of course, transformations between different reference systems can be performed and are in particular described by the target data.

As already mentioned above, the treatment beam arrangement can comprise one or more treatment beams which in turn may comprise at least one, preferably two or more spatially separated sub-beams for at least a time interval during treatment. It is to be noted, that simultaneous treatment of multiple targets by multiple sub-beams allows a significant decrease in treatment time compared with successive treatment of single targets. Therefore, according to the present invention, it is preferred to have a treatment beam which comprises at least two sub-beams which allow simultaneous treatment of at least two targets. The two of the at least two sub beams can be generated from a beam issued from a single treatment beam source, in particular by blocking part of the beam by means of a beam shaping device (for instance a multileaf collimator) in particular for conformal shaping of the treatment beam and/or by using two different sub-treatment beam sources each of which issuing one of the two sub beams (in other words the treatment beam source comprises two sub-treatment beam sources (which in particular can be moved independently or dependently)). A treatment beam can comprise, in particular consist of one or more sub-beams. Preferably, the treatment beam source is movable in order to generate (in particular in combination with a beam shaping device) the treatment radiation (which has spatial and/or time features) in accordance with the treatment plan, i.e. treatment beam arrangement (determined in accordance with the present invention), targets seen from the direction of the treatment beam source may "overlap" for a certain period of time during movement of the beams source, so far spatially separate sub-beams directed to those targets may then merge for that period of time. A sub-beam which results from merged sub-beams which were formerly respectively dedicated to the treatment of just one target treats in particular more than one target, i.e. all the targets which were formerly independently treated by the merged sub-beams. Therefore, the treatment beam can comprise at least two (integral) sub-beams which are spatially separate for at least a time interval during treatment and which can merge for a certain time interval during treatment. The present invention is in particular directed to determine a treatment beam arrangement which is optimized for the treatment of spatially separate targets by means of sub-beams.

By means of the inventive data processing method, a treatment plan (treatment beam arrangement) for simultaneous treatment of a set of at least two targets is determined. That is, preferably at least two targets are simultaneously treated by at least two sub-beams at least during a time interval during treatment. The (radiation therapy) treatment is performed during the time referred to as "treatment time" and corresponds in particular to a treatment session (also called "fraction") which is performed during the treatment time. Since the treatment beam arrangement for simultaneous treatment of the above-mentioned set of at least two targets depends in particular on the set of at least two targets and vice versa, the inventive method comprises in particular the determination of the set of at least two targets for which a treatment beam arrangement can be determined (which fulfils the constraints described by the treatment beam constraint data and the criteria described by the treatment beam position data. The at least two targets comprise in particular only targets which can (potentially) simultaneously be treated for the whole treatment time in accordance with one or more of the potential treatment beam arrangements.

The set of targets to be treated by the treatment beam can be a function of time. In other words, one or more targets of the at least two targets can be "omitted" from the set of targets for at least a time interval/time period during treatment. As will be described in the following, targets which cannot be treated simultaneously with other targets due to technical constraints (treatment beam constraint data) and medical criteria (treatment beam criteria data) can be omitted from the at least two targets at least during a time interval for which such constrains and criteria do not allow simultaneous treatment of this target. Therefore, the set of targets, in particular the coverage individual targets of the at least two targets by the treatment radiation can change over time. The above-mentioned technical constraints are described herein by the above-mentioned "treatment beam constraint data" and the above-mentioned medical criteria are described by the above-mentioned "treatment beam criteria data". The set of targets can in particular comprise during a time interval (i.e. during a part of) the treatment time all of the targets, less than all of the targets, one or more targets or zero targets. The set of targets includes in particular at least during a time interval of the treatment time one or more targets but less than all of the at least two targets.

Particularly, the treatment beam source can move relatively to the targets which, seen from the direction of the beam source, may change the geometry, in particular outline. Preferably, the treatment beam device is constituted to change the "geometry" of cross sectional areas of sub-beams directed to such targets when the treatment beam source is moved in particular so as to make sure that the targets absorb the treatment beam over the whole cross-sectional area from each direction the treatment beam source is directed to the targets. Preferably, the beam is shaped in such a way that, if the at least two targets are projected into a plane (projection plane) perpendicular to the beam direction of a spatially separate one of the one or more sub-beams and if the cross sectional area of the spatially separate sub-beam is projected into the plane, then there lies not more than one of the at least two projected spatially separate targets spatially separate within the projected cross sectional area, in particular at least for not longer than a predetermined time. This criterion (referred to as "not more than one target" criterion) is considered to be an example of the radiation reduction criterion described in more detail below.

In particular, the treatment beam constraint data describe constraints for possible (potential) treatment beam arrangements, in particular describe spatial information on the possible treatment beam arrangements in particular in a reference system in which the treatment device is at rest. The constraints are in particular technical constraints which describe possible relative positions between the beam source and the patient (in particular the targets) which are made possible by the treatment device. The treatment beam constraint data describe in particular information on possible configurations and/or positions of a beam shaping device, particularly a collimator, specifically a multileaf collimator, shaping the cross-sectional shape of the beam, and/or on possible positions of the beam source relative to the at least two targets (e.g. due to a limited range of movement of the beam source for instance along a path and/or a limited range of movement of a couch on which the patient is lying). In other words, such constraints are "technical" constraints which are concerned with the feasibility of generating a treatment beam arrangement. The feasible treatment beam arrangements are referred to herein as "potential treatment beam arrangements". In other words, potential treatment beam arrangements are arrangements which can be realized by the treatment device but which can or cannot violate the medical criteria. It is to be understood that each beam shaping device which forms the cross-sectional shape of the beam generated by the beam source is subjected to certain technical borders for at least a time interval during treatment. For example, a multileaf collimator which can be used as a beam shaping device, is not able to generate separate sub-beams at least part of which lies in a direction parallel to the direction the leaves of the multileaf collimator are moved. Moreover, constraints of features of an arrangement of at least one treatment beam can include information on possible positions of a beam source relative to the at least two targets. For example, one or more target may be located outside of an area which can be covered by means of a treatment beam generated by means of a treatment beam source in a certain position (location and/or orientation) relative to the target/targets, wherein, when the treatment beam source is moved to another position, said target or targets are located within the area covered by the beam.

The treatment beam criteria data in particular relate to medical criteria for treating spatially separate targets. Those criteria in particular describe that parts outside the targets (referred to as "outside body parts") are preferably not affected by treatment radiation due to limited options available in accordance with the treatment beam constraint data. In accordance with the invention, the treatment beam criteria data described below are applied in order to determine the treatment plan. The treatment beam criteria data in particular describe a criterion referred to as "radiation reduction criterion" according to which the exposure of outside body parts to radiation (in the following also referred to as "exposure") is to be reduced, if possible (and in particular if the reduction is more than a predetermined extent) by performing a non-simultaneous treatment instead of a simultaneous treatment of the at least two targets. That is, a reduction (in particular a reduction by the predetermined extent or more) has in particular higher priority than a simultaneous treatment of all of the at least two targets during treatment. "Allowing for the determination of a non-simultaneous treatment plan" means in particular that the reduction of the exposure (of the outside body parts in particular of at least to the predetermined extent) is given higher priority than simultaneous treatment of all of the at least two targets when determining the (optimised) treatment plan. A reduction of exposure means in particular that the volume (filled with outside body parts and not including the at least two targets and also referred to as "healthy volume") and subjected to treatment radiation is to be reduced, if such a reduction can be achieved by non-simultaneous treatment instead of simultaneous treatment and in particular if such a reduction is equal to or more than a predetermined extent. This healthy volume refers in particular to a volume which is or comprises volume inbetween of two or more or all of the at least two targets. The healthy volume can in particular be a volume within a gap between two targets which volume is subjected to treatment radiation if the two targets are treated simultaneously by (only one spatially separate) sub beam. If one wants to treat all of the at least two targets simultaneously for the treatment time (i.e. the total time of treatment), then it can be unavoidable to subject healthy volume between the targets to the treatment radiation due to the constraints described by the treatment beam constraint data. Nevertheless, a reduction of the healthy volume subjected to the radiation would be desirable. According to the radiation reduction criterion it is allowed (that is in particular allowed, in particular preferred, or in particular a must) that a treatment plan (referred to as "non-simultaneous treatment plan") is determined which describes a non-simultaneous treatment if this non-simultaneous treatment results in a reduction of the exposure, in particular in a reduction of the healthy volume (volume filled with outside body parts) subjected to the treatment radiation of the at least one treatment beam, in particular at least in a reduction in a predetermined extent. The non-simultaneous treatment plan which results in the reduction is also referred to as non-simultaneous reduction treatment plan. The term "allowed" means in particular that the non-simultaneous reduction treatment plan represents a potential candidate for a treatment plan to be determined by the treatment plan determining step and is not excluded as a potential candidate for a (optimised) treatment plan. According to an embodiment, the allowance results in the preference of the non-simultaneous reduction treatment plan compared to a simultaneous treatment plan (which results in higher exposure) since the dose criteria data request a low exposure of outside body parts to treatment radiation. According to another embodiment, the term "allowed" encompasses that the non-simultaneous reduction treatment plan is preferred over a simultaneous treatment plan which results in a higher exposure or it is an obligation (must) to choose a non-simultaneous reduction treatment plan instead of a simultaneous treatment plan (which results in higher exposure). In particular the dose criteria data describe the criterion that one of potential treatment plans has to be determined which results in the lowest possible exposure of outside body parts to treatment radiation while the targets are exposed to at least the predetermined dose of treatment radiation. In this way, the allowance of determining a non-simultaneous treatment plan results in the determination of a non-simultaneous treatment plan instead of a simultaneous treatment plan if the non-simultaneous treatment plan is a non-simultaneous reduction treatment plan.

The aforementioned reduction is in particular achieved compared to the case that all of the at least two targets are subjected to the treatment radiation simultaneously during treatment time while in particular both the simultaneous and the non-simultaneous treatment plan fulfil the criteria described by the dose criteria data. In particular, the at least two targets are subjected to the same or higher treatment radiation dose in the case of treatment in accordance with the non-simultaneous treatment plan than in case of treatment in accordance with the simultaneous treatment plan. The non-simultaneous and the simultaneous treatment plan is in particular that one of the plurality of potential simultaneous treatment plans which best fulfils the dose criteria data, i.e. is in particular an optimum simultaneous treatment plan. The radiation volume reduction criterion can be fulfilled by a simultaneous treatment plan if there is no non-simultaneous treatment plan which results in a reduction of the exposure, in particular of healthy volume subjected to treatment radiation at least to a predetermined extent. The radiation volume reduction criterion can be fulfilled by a non-simultaneous treatment plan if the non-simultaneous treatment plan results in the reduction of the exposure, in particular the healthy volume subjected to the treatment radiation at least to the predetermined extent. In other words, the radiation volume reduction criterion is deemed to be fulfilled by a non-simultaneous treatment plan if this non-simultaneous treatment plan results in the reduction of the exposure, in particular the healthy volume subjected to treatment radiation at least to the predetermined extent. The radiation volume reduction criterion is deemed to be fulfilled by a simultaneous treatment plan, if there is no non-simultaneous treatment plan which results in the reduction of the exposure, in particular of the healthy volume at least to the predetermined extent. A violation of the radiation volume reduction criterion means in particular that the determined treatment plan is a simultaneous treatment plan although there is a non-simultaneous treatment plan which would result in less exposure, in particular in less healthy volume subjected to treatment radiation (at least to the predetermined extent).

The non-simultaneous treatment plan describes treatment of not all of the targets for the whole treatment time. That is, one or more of the at least two targets can be omitted during at least a time interval during treatment. Nevertheless, preferably each of the targets is treated at least for one time interval during treatment time. Contrary to this, the simultaneous treatment plan describes simultaneous treatment of all of the targets for the whole treatment time. In particular, the subjection of the healthy volume to treatment radiation is preferably reduced (in particular has to be reduced) at least by a predetermined extent in order to fulfil the radiation reduction criterion. In other words, if the reduction would be less than the predetermined extent, then all of the targets are subjected simultaneously to radiation. Thus, the predetermined extent represents a threshold value which triggers switching between a simultaneous treatment plan and non-simultaneous treatment plan. The predetermined extent can be a predetermined percentage of dose reduction for the healthy volume compared to the case of simultaneous treatment of all of the at least two targets in accordance with the treatment plan or can be a predetermined dose reduction of the dose absorbed by the healthy volume or can be a reduction of time, during which the healthy volume is subjected to the treatment radiation or can be a predetermined percentage defined by dividing the reduced volume by the total healthy volume, the reduced volume being the healthy volume which is avoided to be subjected to treatment radiation if switching from the simultaneous treatment plan to the non-simultaneous treatment plan. Of course further examples for defining the predetermined extent are possible. As mentioned above, the healthy volume can be defined to be the healthy volume inbetween all of the at least two targets. The healthy volume can for instance be defined by a geometrical body which encompasses all of the at least two targets and which is in particular inside the patient's body, the geometrical body can for instance be a sphere or a cuboid and can in particular be defined to be that one out of a plurality of possible geometrical bodies (of one or more types) which has the smallest volume but nevertheless encompasses all of the at least two targets. The healthy volume can also be defined to be the total volume inside the patient subjected to radiation with the exception of the volume occupied by the at least two targets.

The radiation volume reduction criterion is in particular defined to request reduction of the healthy volume of the patient's body by determining a non-simultaneous treatment plan instead of a simultaneous treatment plan if the non-simultaneous treatment plan results in less exposure, in particular less healthy volume subjected to treatment radiation at least to a predetermined extent than the simultaneous treatment plan. In particular, if the non-simultaneous treatment plan results in less exposure, in particular less healthy volume subjected to treatment radiation at least to a predetermined extent, then the at least one treatment beam cannot pass simultaneously through all of the at least two targets at least for a time interval during treatment in order to fulfil the radiation volume reduction criterion. In particular, the radiation volume reduction criterion requests that a treatment plan (which is to be determined) describes a non-simultaneous treatment of the at least two targets at least for a time interval during the treatment time if the treatment plan to be determined describes a non-simultaneous treatment according to which, in particular at least to a predetermined extent, less exposure, in particular less healthy volume of the patient's body is subjected to treatment radiation compared to the case of a treatment in accordance with another treatment plan which describes simultaneous treatment of the at least two targets during the treatment time.

The predetermined extent can be a combination of one of the aforementioned examples, further examples are possible. In particular, the predetermined extent can be a function of the increase of treatment time which results from a non-simultaneous treatment plan (which describes the non-simultaneous treatment) compared to the simultaneous treatment plan (which describes the simultaneous treatment). In particular, the required predetermined extent can be the higher the higher the increase of treatment time is if the non-simultaneous treatment plan is chosen instead of the simultaneous treatment plan. The simultaneous treatment plan is in particular determined by reducing the amount of healthy volume subjected to treatment radiation as best as possible while still simultaneously treating all of the at least two targets. With respect to the minimization a reference is made to the article "A method for optimizing LINAC treatment geometry for volumetric modulated arc therapy of multiple brain metastases; Med. Phys. 37(8), August 2010.

The aforementioned volume reduction criterion is preferably described and in particular represented by referring to the one or more sub beams. In particular, the aforementioned exposure, in particular the amount of healthy volume subjected to radiation can be reduced and/or is deemed to be reduced if there is not more than one target treated by one of the sub beams which is spatially separate to the other sub beams. This means in more detail that, if viewed from the perspective of the spatially separate sub beam, no spatially separate targets should be covered by the spatially separate sub beam but preferably just one target is covered by the spatially separate sub beam. In other words, if projecting the at least two targets into a plane perpendicular to the (beam direction of the) spatially separate one of the one or more sub beams and if projecting the cross section area of the spatially separate sub beam into the same plane, then there preferably lies not more than one of the at least two projected spatially separated targets spatially separate from each other within the projected cross sectional area. On the other hand, the exposure, in particular the healthy volume subjected to treatment radiation is increased if the projected cross section covers two or more projected targets which are spatially separate in the plane (referred to as "projection plane"). In this case, the volume between the two or more targets is subjected to treatment radiation. The term "spatially separate sub beam" means that the sub beam is integral, in particular has no contact to other sub beams, in particular the projected cross sectional area of the spatially separate sub beam does not overlap with a projected cross sectional area of another sub beam. In particular if two or more sub beams merge during treatment in accordance with the treatment plan, and this results in the aforementioned overlap, then the two or more sub beams are treated to be one new spatially separate sub beam. According to an embodiment, there is a defined minimum distance which the projected targets have to have in the projection plane in order to be considered to be "spatially separate" in the projection plane. This minimum distance can be a predetermined minimum distance which is for instance higher than 1 mm or 5 mm and less and 10 cm or 5 cm. This minimum distance can be a function of, in particular can correspond to the minimum distance which can be achieved by the treatment device, in particular by the beam shaping device between two neighbouring spatially separate sub-beams. For instance, in case a collimator is used for beam shaping, the minimum distance is for instance the distance caused between two sub beams if just one leave is inbetween the sub beams or a function of this distance like this distance multiplied by a predetermined factor (which is in particular higher than 0.1 or 0.3 and less than 3 or 10. In view of this, the aforementioned criterion is described for spatially separate sub beams. Preferably, treatment plan is determined which allows for simultaneous treatment of all of the at least two targets during the treatment time (i.e. during the total treatment time). However, a non-simultaneous treatment of the at least two targets is allowed, in particular preferred, in particular has to be performed if the aforementioned criterion (of not more than one target within a cross sectional area of spatially separate sub beam) cannot be fulfilled otherwise. As mentioned above, the reduction of subjection of healthy volume to treatment radiation should be at least to the above-mentioned predetermined extent in accordance with an embodiment. Applying this to the "not more than one target" criterion (see criterion a in claim 2), this means that note more than one target (in particular at least for not for longer than a predetermined time) is treated by a spatially separate sub beam according to an embodiment. In other words, the "not more than one target" criterion is considered to be only violated if more than one projected target is covered (continuously) by the projected cross sectional area of the spatially separate sub-beams for more than the predetermined time. Also this predetermined time can be a function of the extension of treatment time which can result from choosing the non-simultaneous treatment plan instead of a simultaneous treatment plan. The predetermined time can also be a fixed time which be zero or more, in particular can be longer than 0.1 second or 1 second and which can be shorter than 10 seconds or one minute. The predetermined time can also be a percentage of the time of simultaneous treatment of two targets by one spatial separate sub beam in accordance with the simultaneous treatment plan. The predetermined time can also be a function of the dose to be additionally absorbed by healthy volume until the predetermined time is reached compared to the case the predetermined is set zero.

As mentioned above, the radiation reduction criterion can be represented by the "not more than one target" criterion according to an embodiment of the invention. This embodiment therefore consists of or comprises the following features:

A data processing method for determining a treatment plan for radiation therapy treatment of at least two spatially separate targets by means of a treatment device constituted to treat the at least two target by means of one or more sub-beams during treatment time, the one or more sub-beams constituting at least one treatment beam which is to pass through the at least two targets in accordance with a treatment plan during treatment time, the treatment device being further constituted to allow for simultaneous treatment of the at least two targets by at least two of the sub-beams at least during a time interval during treatment time, the method comprising the following steps performed by a computer:

acquiring target data describing spatial information on the at least two spatially separate targets in a patient's body;

acquiring treatment beam constraint data which allow determination of potential treatment plans which can be realized by the treatment device and which potential treatment plans describe potential arrangements of the at least one treatment beam, referred to as potential treatment beam arrangements;

acquiring treatment beam criteria data describing criteria for the treatment of the at least two targets by the at least one treatment beam, the criteria comprising a radiation reduction criterion which describes that a treatment plan is allowed to be determined which describes the following criteria a) and b):

a) the criterion a) describing that, if projecting the at least two targets into a plane perpendicular to a spatially separate one of the one or more sub-beams and if projecting the cross sectional area of the spatially separate sub-beam into the plane, then there lies not more than one of the at least two projected spatially separate targets spatially separate, in particular by at least a predetermined distance, within the projected cross sectional area, in particular at least for not longer than a predetermined time; and b) the criterion b) allowing that the treatment plan describes that the at least one treatment beam does not pass simultaneously through all of the at least two targets at least for a time interval during treatment in order to fulfil the criteria a), wherein in particular this is only allowed if this results in a reduction of the healthy volume subjected to treatment radiation at least to a predetermined extent.

If a non-simultaneous treatment plan is determined in order to fulfil the treatment beam criteria data, then not all of the targets are treated simultaneously for the whole of the treatment time. In particular, if no simultaneous treatment plan can be found which fulfils the radiation reduction criterion and/or, in particular if there is a (candidate) non-simultaneous treatment plan which fulfils the radiation reduction criterion, in particular then the targets which are subjected to treatment at a specific time during treatment are preferably described by a set of targets. This set of targets can be function of time which time is within treatment time. The treatment plan is preferably determined based on the set of targets, that is according to an embodiment of the invention, the acquisition of the set of targets can be a step before determination of the treatment plan or according to another embodiment of the invention, the set of targets is determined during determining the treatment plan (for instance by using interactive steps). The set of targets can be acquired by determining the set such that each of the at least two targets is treated at least for a time interval of the treatment time, in particular so that each of the targets is subjected to the required treatment dose required for one treatment session (which required dose is described by the above-mentioned dose criteria data which are in particular comprised by the target beam criteria data).

As mentioned above, a simultaneous treatment plan is preferred. If this is not possible without violating the radiation reduction criterion, the number of targets within the set of targets is preferably maximized (in particular for any time during treatment time) in particular in order to minimize the total treatment time. Preferably, the treatment beam criteria data describe this maximization criterion. Preferably, the treatment beam criteria data also describe that the treatment plan, in particular the set of targets is determined so that the treatment time is minimized. This determination is preferably performed based on the target data, the treatment beam constraint data and the treatment beam criteria data. The determination of the treatment plan is preferably performed by using optimisation algorithms which in particular vary parameters of potential treatment beam arrangements (like beam positions and/or treatment time) and/or the set of targets (see below) in order to find the optimised treatment plan.

The treatment plan can be determined by generating a plurality of candidate treatment plans which describe potential treatment arrangements. Then, for each of the candidate treatment plans it is checked whether they fulfil the treatment beam criteria data. That one which fulfils the criteria best is selected as the determined treatment plan.

As mentioned above, the determination of the treatment plan can be based on the set of targets which is determined before the final determination of the treatment plan. According to an embodiment, the set of targets is determined by determining a candidate set. The candidate set is determined by omitting one or more of the at least two targets during a first time interval during the treatment time and by including the omitted one or more of the at least two targets into the candidate set during a second time interval outside the first time interval. Then it is checked whether a treatment plan can be determined for the candidate set which fulfils the treatment beam constraints data and the treatment beam criteria data. If a treatment plan can be determined, then the determination of the treatment plan is achieved. If a treatment plan cannot be determined, a new candidate set is generated and the preceding steps are repeated by varying the time intervals and/or by varying the omitted targets.

The aforementioned omission of targets can be in accordance with a brute-force optimisation algorithm which varies all possible options in order to find the set of targets which best fulfils the treatment beam criteria. Alternatively targets can be omitted during which the radiation reduction criterion and in particular the "not more than one target" criterion is violated if treatment is performed in accordance with the simultaneous treatment plan. Thus, the simultaneous treatment plan which violates the "not more than one target criterion" can be used in order to identify the violation time interval and in order to identify those (more than one) targets (referred to as "violation targets") which are involved in the violation of this criterion, i.e. the spatially separate projections of which are covered by the projection of a cross section of one spatially separate sub beam. Thus, according to an embodiment, preferably at least one of those violation targets is omitted for the violation time in order to find the candidate set and at least one of the violation targets is for instance included in the set of targets as exclusive or non-exclusive member of the set after the non-omitted targets have been subjected to the treatment radiation in particular in accordance with the dose criteria data describing the dose criteria for the non-omitted targets and/or in particular before or after a change of the treatment path (e.g. the rotation of the patient; see below) has been performed.

According to an embodiment, the set of targets which is a function of time is described as a sequence of sub sets which is to be treated one after the other. Each sub set in particular consist of fixed targets which are treated during a time interval. That is, the targets subjected to treatment are not changed during this time interval and in particular all targets of the sub set are simultaneously treated during the time interval. The treatment plan is preferably determined by combining sub-treatment plans which are to be performed one after the other during the treatment time in order to subsequently treat the sub sets. In other words, each sub-treatment plan describes the treatment of one sub set for a time interval (also referred to as "sub-treatment time"). The sub treatment plans are determined based on the spatial information on the targets of the sub sets, the treatment of which they describe. The spatial information is acquired from the target data. Thus, the sub treatment plans are determined based on the target data, the treatment beam constraint data and the treatment beam criteria data. The sub sets are preferably selected so that a combination of the sub-treatment plans (i.e. the determined treatment plan) results in treatment of all of the targets of the at least two targets which treatment in accordance with the determined treatment plan fulfils in particular the dose criteria data while sub-treatment plans can be but have not to be obliged to fulfil the dose criteria data for the targets of the subset. In particular, a dose required for one of the targets according to the dose criteria data can be achieved by combining sub-treatment plans. Since the sub sets can but do not have to include less targets than all of the at least two targets (and preferably comprise more than zero targets, in particular more than one target), determination of a sub-treatment plan which allows for simultaneous treatment of all of the targets of the sub set while fulfilling the treatment beam constraint data the radiation reduction criterion for the targets of the sub set is more likely to be achievable than a treatment plan which has to describe treatment of all of the targets and which has to fulfil the treatment beam criteria data and the radiation reduction criterion. The time interval during which the treatment is performed in accordance with a sub treatment plan is also referred to herein as sub-treatment time. The sub treatment plans preferably fulfil the radiation reduction criterion, in particular the "not more than one target" criterion for all of the targets of the subset but not necessarily for all of the at least two targets which are to be treated. The fulfillment of the radiation reduction criterion by a sub-treatment plan means in particular that by omitting a further target of the subset a reduction of the healthy volume (in particular at least to predetermined extent) which is subjected to radiation, cannot be achieved.

The treatment device preferably comprises a beam source which is movable relative to the at least two targets. The movement of the beam source is in particular constrained in that it has to move along a path in particular in order to deliver an arc of conformal radiation. In particular, the only movement of the patient during treatment is a rotation of the patient. The relative position of the path relative to the patient can change e.g. by the aforementioned rotation. The path which can change its position relative to the patient and which is described in a reference system in which the at least two targets are at rest is referred to as "treatment path". Thus the treatment path can change due to movement of the patient. The path which is described in a reference system in which the treatment device is at rest is described as "device path". The device path does not change if the patient is moved. The path can have in particular an arc shape, i.e. the beam sources moves along the arc. The movement is in particular from a starting point to an end point in one direction and then from the end point back to the start point in opposite direction. Both of these movements are referred to as complete movements. The issue of radiation can be performed during the complete movement only when the beam source is within one or more sections of the path or for the (whole) path. The section can differ depending on forward movement or backward movement of the beam source. The aforementioned sub-treatment plans can in particular describe the treatment for a section of the path or for the path (i.e. the full path). The sub treatment plans are in particular related to movements of the beam source where there is no change of direction of movements. Thus, for instance a first sub treatment plan relates to an arc section of e.g. 0-30°, a second sub treatment plan relates to a subsequent arc section of e.g. 30-60° and a third sub treatment plan relates to a further subsequent arc section to e.g. 60-90° and a fourth arc section relates to a backward movement of the beam source along an arc section from e.g. 60° to 30°. While for instance the first and third sub set includes all of the at least two targets, the second sub set omits one or more of all of the at least two targets. By the omission, the second sub treatment plan can fulfil the radiation reduction criterion. Then, for instance the fourth sub treatment plan describes treatment of the omitted one or more targets in order to complete treatment of all targets. By omitting targets during a forward movement along a path and by treating omitted targets during a backward movement along the same path, the treatment time can be minimized. The aforementioned arc sections represent just examples.

According to an embodiment, the subsets are assigned to one path (i.e. the full path from a starting point of the device path to an end point of the device path). Thus, the beam source moves along the device path in order to treat one of the subsets and repeats such a (for instance forward or backward movement) until all subsets are treated which means that all of the targets of the at least two targets have been treated. For instance, during a first movement along the device path, a first subset is treated. Then, during a second movement of the device path, a second subset is treated which includes as many as possible of the targets omitted from the first subset while still complying with the radiation reduction criterion. If necessary, a third subset or more subsets are treated during subsequent movements of the beam source along the device path in order to finally treat all targets. Preferably a change of the treatment path (e.g. by rotation of the patient) is only performed after all of the targets of the at least two targets have been treated at least for a time interval, in other words only after each of the at least two targets was a member of one of the treated subsets.

A section of a path where targets are omitted are referred to herein as omitting section and a section of a path where the omitted targets are treated are referred herein as supplementing section. According to an embodiment, the omitting section is described by a sub treatment plan which describes a treatment by moving the beam source in a first direction (e.g. forward) and a supplementing section is described by a sub treatment plan which describes a treatment by moving the beam source in a second direction (e.g. backward). The terms backward moving and forward moving are freely exchangeable herein. The first and second direction can be the same or can be different, in particular opposite. According to a particular embodiment, the omitting section and the supplementing section differ from each other if those sections belong to the same treatment path. According to another embodiment, there are different treatment paths for a forward movement and a backward movement of the beam source. In particular, the different treatment paths are realized by a movement of the at least two targets (i.e. of the patient's body) in a reference system in which a first path along which the beam source moves is at rest. The movement is in particular a rotational movement. For instance, the beam source is moved along an arc of the device path which describes the first treatment path. Then the patient is rotated. Then the beam source moves backward along the same arc of the same device path but due to the rotation of the patient, the second treatment path differs from the first path. Please note that the term treatment path relates to a relative position between the patient and the at least two targets. Thus, the position of the arc of the device path in a reference system in which the treatment device is at rest does not change while the position of the corresponding treatment path (e.g. arc) in a reference system in which the patient is at rest changes due to the rotation of the patient in the reference system in which the treatment device is at rest. Preferably, in this case, the omitting section and the supplementing section would be the same if there were no relative movement of the at least two targets in the reference system in which the treatment device is at rest, i.e. in which the one or more possible device paths are at rest. In particular, due to the rotation of the patient different directions of incidence of the sub beam are possible which allow to fulfil the treatment beam criteria data. It is just an option that the omitting section and the supplementing section are identical sections of the device path, they can of course also be different. In particular, the end point of the first treatment path is preferably identical with the starting point of the second treatment path in order to reduce the treatment time.

In particular, the determination of one of the sub sets and/or one of the sub-treatment plans depends on other already determined sub-sets and/or sub-treatment plans used for the determination of the treatment plan in order to stepwise determine the sub-sets and finally the set of targets.

Since, as already mentioned above, beam generation is subjected to certain technical constraints, certain arrangements of targets cannot be treated with certain configurations of a treatment beam source and a beam shaping device. For example, if at least two of the at least two targets are located in a direction parallel to the movement direction of the leaves of a multileaf collimator, it can be not possible to direct sub-beams to each of the targets without directing at least part of the sub-beam to healthy volume located between the at least two targets. However, such situations should be avoided as far as possible so as to keep the exposure to radiation for the patient as low as possible.

According to another preferred embodiment of the present invention, at least one particularly vertical plane is defined for a preferably arc-shaped relative movement of the beam source (along a treatment path) with respect to the at least two targets, wherein for at least one plane at least one sub-treatment beam arrangement is determined, wherein targets which are omitted entirely and/or for at least one interval of the treatment time from a foregoing subset of targets are assigned to a subsequent set of targets, until each target is contained in at least one of the at least one subset of targets, and wherein a possible last subset of target is determined comprising one remaining target. It will be understood that if one target remains which cannot be assigned to any subset of targets, a further subset of targets comprising this target only must be determined so as to make sure that every target it is assigned to a subset of targets for treatment of the targets by means of the treatment beam.

In other words, each defined, particularly vertical plane comprises at least one subset of targets which are determined by method steps described above. Determining the at least one subset of targets for a plane can depend or can be independent from the determination for at least one subset of targets determined for another plane.

If the beam source is moved along a straight line, or preferably along an arc-shaped pathway, a certain time interval relates to a certain sector or angle which is covered by the beam source during this time. Therefore, a target is omitted during a certain time interval of treatment, it can be said that this target is omitted for a certain treatment distance or treatment-angle. In other words and according to this preferred embodiment of the present invention, only treatment angles are considered for which at least one target has been omitted for a foregoing plane. For example, if a target is omitted for a certain distance or angle in a plane, only this distance or angle will be covered by the beam source in a following plane. This allows for further reduction of treatment time, since the beam source only covers the considered distance or angle in plane, for which angle or distance a target has been omitted in a foregoing plane, particularly the directly foregoing plane.

According to a further preferred embodiment, control data is provided comprising information on the at least one determined treatment beam arrangement and/or the at least determined set of at least two targets for at least one plane, particularly, comprising information to successively treat at least one determined set of targets of at least one plane by means of the at least one respectively determined treatment beam arrangement. In other words, control data is determined based on the determined treatment plan (treatment beam arrangement) for simultaneous treatment of a set of at least two targets by the arrangement. This control data is configured to generate control signals for controlling at least one of a couch and a treatment device comprising a beam shaping device and beam source as described further below. More generally spoken, control data is configured to generate control signals for controlling any device which directs a beam which may comprise at least two sub-beams to a target, move the beam relatively to the target and shape the cross-sectional area of the beam accordingly.

A further aspect of the present invention refers to a program, which when running on a computer, causes the computer to perform the method according to any one of the preceding claims and/or to a program storage medium on which the program is in particular non-transitory stored and/or a computer on which the program is running or into the memory of which the program is loaded and/or a signal wave, in particular a digital signal wave, carrying information which represents the program, in particular, the aforementioned program in particular comprises code means adapted to perform all the steps of the method of one of the preceding claims.

A further aspect of the present invention refers to a radiation therapy system, comprising:
the computer (1) of the preceding claim;
a couch (2) for placing a patient (6);
and a treatment device (3) comprising the beam shaping device (4) and the beam source (5);
wherein the treatment device (3) and the couch (2) are movable relatively to each other, particularly wherein the couch (2) is rotatable in a horizontal plane and/or the treatment device (3) is movable along an arc-shaped pathway lying in a specifically vertically oriented plane.

In the following example embodiment of the present invention are described as reference to the figures which are merely to be regarded as examples of the invention without limiting the invention of these specific embodiments.

Figure 2:
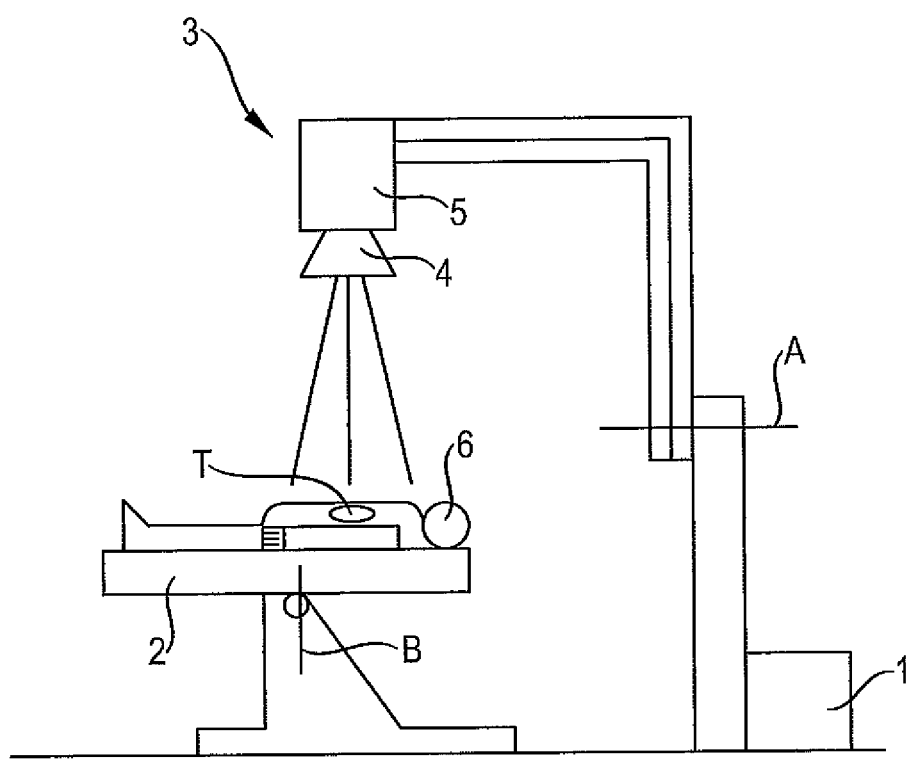
Figure 3:
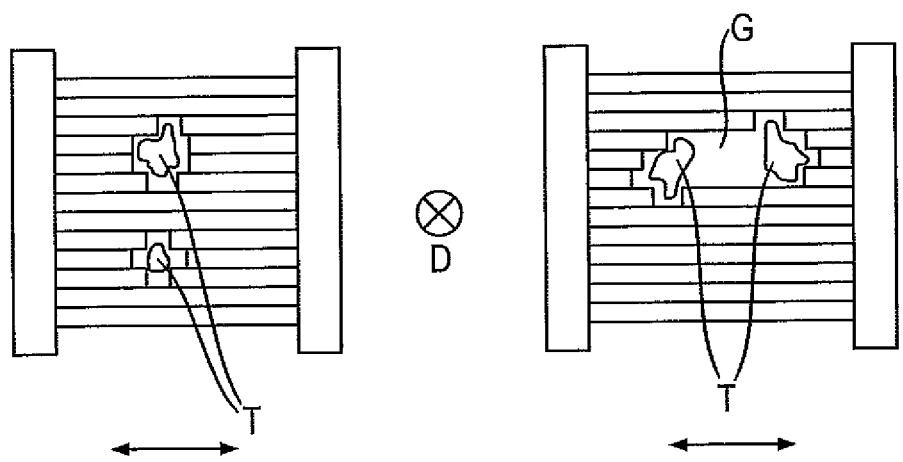
Figure 4:
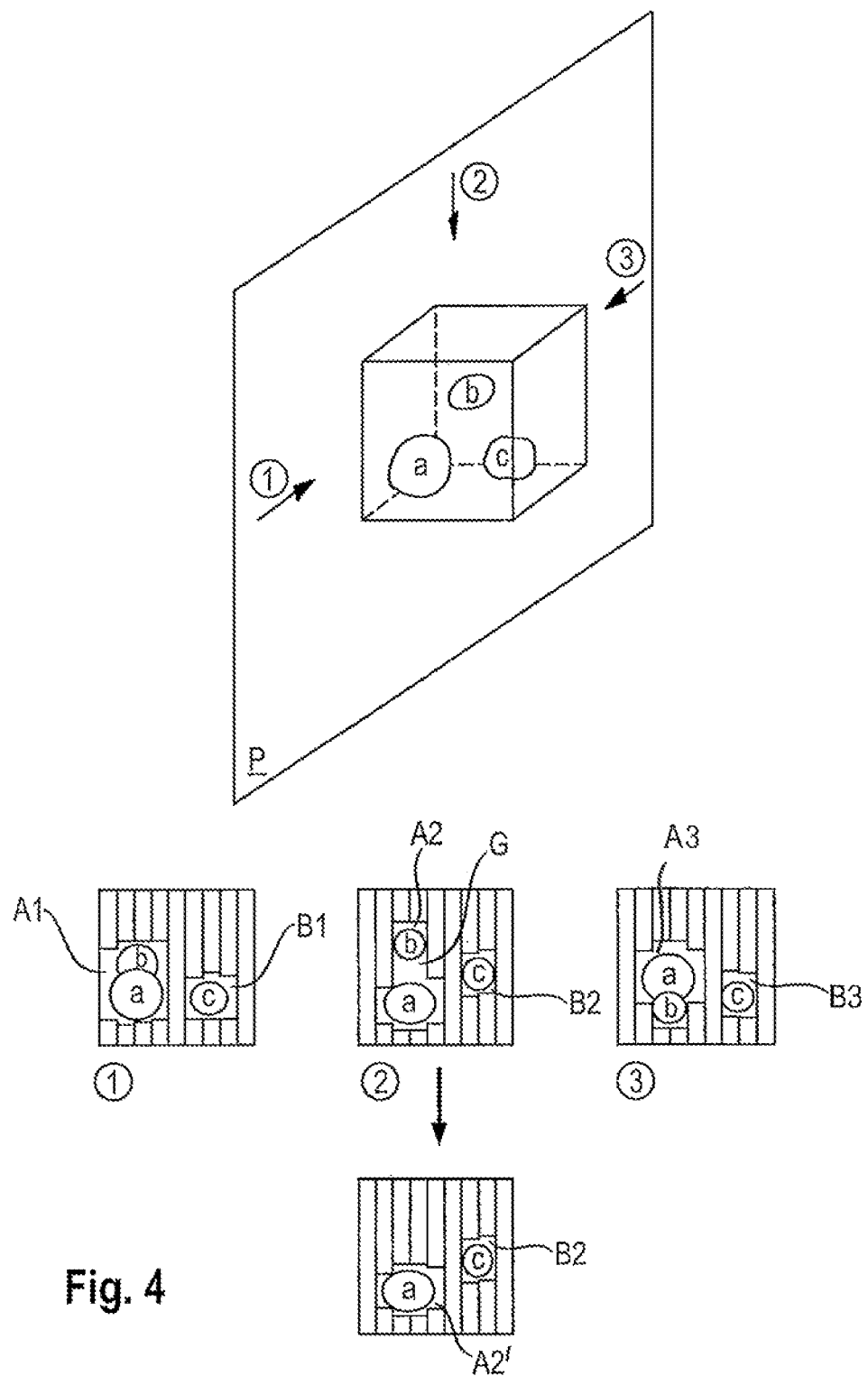

FIG. 1 shows an exemplary flow diagram of the method in accordance with the present invention;
FIG. 2 shows an exemplary embodiment of a radiation therapy system in accordance with the present invention;
FIG. 3 shows two configurations of a multileaf collimator;
FIG. 4 shows three targets seen from different directions.

As can be seen in FIG. 1 target data, treatment beam constraint data and treatment beam criteria data is acquired as constraints for determining a treatment plan for simultaneous treatment of a set of at least two targets by a treatment plan, wherein target data describes spatial information of the targets to be treated in a patient's body, treatment beam constraint data describes possible treatment beam arrangements and treatment beam criteria data describes criteria for the treatment of the targets. If it is not possible to treat all targets by one treatment beam arrangements without violating treatment-criteria, one or more of the targets causative for the violation are omitted from the candidate subset of targets, thereby obtaining a subset of targets comprising targets which can be treated simultaneously by a given treatment beam arrangements, wherein, from the subset of targets, a sub-treatment-plan can be determined for treatment of the subset of targets. Since the omitted target (or more omitted targets) will not be treated together with the previously determined subset of targets, at least one further subset of targets is preferably determined containing the omitted target/targets, wherein further sub-treatment-plans are determined from the further subsets of targets.

By combining the determined sub-treatment-plans, a treatment plan for all targets is determined.

Moreover, based on the treatment plan which has been determined, control data can be provided which is configured to generate control signal for controlling at least one device which shapes the cross-sectional shape of the beam (in particular of the sub-beams) and/or the relative position of the beam (in particular sub-beams) with respect to the targets, such as a movable beam source, a beam shaping device like a (movable, in particular rotatable) multileaf collimator and/or a couch for placing a patient.

FIG. 2 shows an embodiment of the inventive radiation therapy system comprising a computer 1 on which a program is loaded which causes the computer to perform the inventive method, particularly to control the treatment device 3 comprising a beam shaping device 4 and a beam source 5, and a couch 2 on which a patient 6 is placed.

It can be seen from FIG. 2 that the treatment device 3 can be moved in a vertical plane along an arc-shaped path of movement around an axis A so as to move around the patient 6 lying on a couch 2.

The beam source 5 generates a radiation beam comprising at least two sub-beams directed to a plurality of targets T in the body of the patient 6. The cross-sectional area of the beam/sub-beams is formed by the beam shaping device 4 in particular so that each sub-beam is assigned for treatment of one (or more) of the targets T. The treatment device 3 is moved along a predefined distance on its path of movement around the patient, while the beam source 5 generates a beam for treating targets T. After a first subset of targets is treated by the beam, a second and further subsets of targets T may be treated by a beam. According to an embodiment, after all targets T have been treated by the beam, the couch 2 is rotated around axis B so as to change the relative position between the patient 6 and the treatment device 3. This is referred to herein as determining a new plane for the treatment device. According to another embodiment, the rotation of the couch is performed before all targets are treated and in the at least one further plane, targets can be treated which have not been treated in the forgoing planes.

FIG. 3 shows two configurations of a multileaf collimator, the leaves of which can be moved in a horizontal direction indicated by arrows. The multileaf collimator is to shape a treatment beam which extends in the direction D perpendicularly to a plane of projection.

Since the targets T to be treated by a beam shaped by the left configuration of the multileaf collimator (shown in FIG. 3) do not overlap in the direction of movement of the leaves, the multileaf collimator is able to shape the beam so as to treat each target T by a spatially separate sub-beam. Thus the healthy volume subjected to treatment radiation is minimized and reduced compared to the right configuration shown in FIG. 3.

As can be seen in the right configuration of the multileaf collimator (shown in FIG. 3), targets T overlap in a direction of movement of the leaves, so that a gap G occurs between the targets T which would lead to absorption of the beam shaped by the multileaf collimator by healthy volume located between the two targets T. In order to avoid such a situation, the multileaf collimator can be rotated around an axis parallel to a direction D (in order to get the above-described left configuration) so that the two targets do not overlap in a direction of movement of the leaves (in this case turning the multileaf collimator by 90 Degrees would prevent such a situation). If such a rotation is not possible this would be described by the treatment beam constraint data and one of the two targets T would be omitted to obtain a first subset of targets and the other would be included in a second subset of targets in order to fulfil the radiation reduction criterion.

FIG. 4 shows a plurality of targets a, b and c which are to be treated by a treatment beam. Targets a, b and c represent the treatment body part and are contained within a volume formed like a cube which represents a patient's body. Moreover, a plane P can be seen in which a treatment beam source can be moved so as to direct a treatment beam towards the targets a, b and c substantially within the plane P. Assuming that the collimator leaves can be moved parallel to the plane P (vertically in position 1) and the treatment beam is directed to the targets a, b and c from direction 1. A first sub-set of targets a, b and c can be treated without violating the "not more than one target" criteria during a first sub-treatment time interval. The leaves define a first cross-sectional area A1 of a first sub-beam and a second cross-sectional area B1 of a second sub-beam. The first and second sub-beam constitute the treatment beam. Thus, the first sub-beam treats the targets a and b. However, those targets are overlapping and are not apart from each other which means that the "not more than one target" criterion is not violated. The same applies for the second sub-beam which treats just one target, i.e. the target c. However, when the treatment device is moved in a clockwise direction to position 2, targets a and b are arranged in such a way that the collimator leaves (which can only be moved in a direction parallel to the plane P) are not able to form so-called islands around every target. That is the cross-sectional area A2 covers the spatially separate targets a and b. Even if the collimator could be rotated by an angle around an axis normal to FIG. 4, it is not possible to individually treat every target by a respective sub-beam without violation of the radiation reduction criterion. As can be seen in FIG. 4 the collimator leaves, when the treatment beam is directed towards the targets a, b and c from direction 2, cannot be moved in such a way that the gap G between targets a and b is covered by means of the collimator leaves. However, such a treatment of targets a, b and c from direction 2 would violate the radiation reduction criterion, since unnecessary absorption of the treatment beam by the healthy volume occurs. In more detail, the targets a and b are spatially separate within the cross-sectional area A2 of a first sub-beam and therefore the "more than one target" criterion is violated for the targets a and b at least for a second sub-treatment time interval which corresponds to the violation time.

Violation of the radiation reduction criterion can be overcome by "omitting" one of violation targets a or b for the violation time. In this example, target b is omitted for the time period in which criteria data is violated, which also can be seen at the bottom of FIG. 4. Thus the second subset consists only of targets a and c which are respectively covered by the cross-sectional areas A2' and B2. When the treatment device is moved further along its path of movement to direction 3, the collimator leaves can be moved to form an island around targets a and b the projections of which overlap in the plane of the cross-sectional area A3. Thus the radiation reduction criterion is not violated. Thus there is a first subset of targets consisting of targets a, b and c for a first treatment time interval which comprises treatment from direction 1. Furthermore, there is a second sub set of targets consisting of targets a and c for a second sub-treatment time interval which comprises treatment from direction 2. There is a third sub set of targets consisting of targets a, b and c for a third treatment time interval which comprises treatment from direction 3.

It is well understood that target b which has been omitted for the time interval of treatment time in which a violation of the treatment beam criteria occurs, has merely absorbed a fraction of the treatment beam energy compared with targets a and c. Therefore, target b can be assigned to a further subset of targets (fourth subset) so as to be treated during a fourth sub-treatment time interval when the treatment device is moved back from position 3 to position 1, for example. Alternatively, targets which have been omitted from a set of targets, for example target b, can be assigned to a subset of targets which is treated during a second movement of a treatment device from position 1 to position 3. Further alternatively targets which have been omitted from a foregoing set of targets can be treated after the targets have been rotated relatively to the vertical plane P, particularly by rotating the patient around a vertical axis. By such a rotation, a new plane P different from the first plane P is defined, in which the treatment device can be moved along a path of movement.

Preferably, the omitted targets such as target b are treated for a time interval or a respective part of the device path of movement of the treatment device, for example an arc section which corresponds to the time interval or the respective part of the path of movement of the treatment device, for example an arc section, for which the target or the targets have been omitted previously.

In other words, the present invention comprises also the following:

A process for radiation treatment of multiple lesions of a single patient without moving the patient other than rotating the patient, utilizing a beam shaping device able to deliver an arc of conformal radiation, using the following steps:

Selecting for each arc a subset of lesions that do not overlap in the direction of the movement of the leaves of the beam shaping device so that in conforming to the leaves to the subset of lesions no undesired exposure of healthy tissue is achieved, then treat these lesions with a conformal arc, repeat the set of selecting a subset of lesions from the remaining untreated lesions with subsequent conformal arc treatments until no untreated lesions are left for that arc plane and proceed with a new couch angle. Preferably, lesions are only selected for the next arc plane for a subset of the angles of the treatment arc where the overlap occurs to reduce the angular range and associated treatment times. Preferably, the couch angle is changed for additional subsets of lesions from the original angle to obtain a better distribution of entry doses over normal tissue. Preferably, the collimator angle is optimized to include all lesions in a single conformal arc. Preferably, the collimator angle is optimized to minimize the number of arc planes or their angular range.

The invention claimed is:

1. A data processing method for determining a treatment plan for radiation therapy treatment of at least two spatially separate targets by means of a treatment device constituted to treat the at least two targets by means of one or more sub-beams during a treatment time, the one or more sub-beams constituting at least one treatment beam which is to pass through the at least two targets in accordance with a treatment plan during the treatment time, the treatment device being further constituted to allow for simultaneous treatment of the at least two targets by at least two of the sub-beams at least during a time interval during the treatment time, the method comprising the following steps performed by a computer:

acquiring target data describing spatial information on the at least two spatially separate targets in a patient's body;

acquiring treatment beam constraint data which allow determination of potential treatment plans which can be realized by the treatment device and which potential treatment plans describe potential arrangements of the at least one treatment beam, referred to as potential treatment beam arrangements;

acquiring treatment beam criteria data describing criteria for the treatment of the at least two targets by the at least one treatment beam, the criteria comprising a radiation reduction criterion which describes that a treatment plan is allowed to be determined which describes a non-simultaneous treatment of the at least two targets at least for a time interval during the treatment time if this treatment plan describes that parts of the patient's body outside the at least two targets are less exposed to treatment radiation, in particular at least to a predetermined extent, compared to the case of a treatment plan which describes a simultaneous treatment of the at least two targets during the treatment time; and determining the treatment plan which fulfils the radiation reduction criterion based on the target data, the treatment beam constraint data and the treatment beam criteria data.

2. The method of claim 1, wherein the radiation reduction criterion comprises the following criteria a) and b), in particular is represented by the following criteria a) and b):

a) the criterion a) describing that, if projecting the at least two targets into a plane perpendicular to a spatially separate one of the one or more sub-beams and if projecting the cross sectional area of the spatially separate sub-beam into the plane, then there lies not more than one of the at least two projected spatially separate targets spatially separate, in particular by at least a predetermined distance, within the projected cross sectional area, in particular at least for not longer than a predetermined time; and b) the criterion b) allowing that the treatment plan describes that the at least one treatment beam does not pass simultaneously through all of the at least two targets at least for a time interval during treatment in order to fulfil the criteria a), wherein in particular this is only allowed if this results in a reduction of the exposure of the parts of the patient's body outside the at least two targets at least to the predetermined extent.

3. The method according to claim 2 wherein, in particular if no treatment plan can be determined which describes the simultaneous treatment and fulfils the radiation reduction criterion, in particular if the at least one treatment beam cannot pass simultaneously through all of the at least two targets during treatment in order to fulfil the radiation reduction criterion, in particular then the treatment plan is determined based on a set of targets, the set of targets describing targets selected out of the at least two targets for the simultaneous treatment by the at least one treatment beam as a function of time and wherein each of the at least two targets is selected at least for a time interval of the treatment time and wherein at least for a time interval during treatment time not all of the at least two targets are selected.

4. The method of claim 3, wherein the number of the targets in the set of targets is maximized for determining the treatment plan based on the target data, the treatment beam constraint data and the treatment beam criteria data.

5. The method of claim 3, wherein the set of targets is determined so that the treatment time is minimized based on the target data, the treatment beam constraint data and the treatment beam criteria data.

6. The method of claim 1, wherein, in particular if no treatment plan can be determined which describes the simultaneous treatment and fulfils the radiation reduction criterion, in particular if the at least one treatment beam cannot pass simultaneously through all of the at least two targets during treatment in order to fulfil the radiation reduction criterion, in particular then the treatment plan is determined based on a set of targets, the set of targets describing targets selected out of the at least two targets for the simultaneous treatment by the at least one treatment beam as a function of time and wherein each of the at least two targets is selected at least for a time interval of the treatment time and wherein at least for a time interval during treatment time not all of the at least two targets are selected;

wherein the set of targets is determined by determining a candidate set, the candidate set being determined by omitting one or more of the at least two targets during a first time interval during the treatment time, by including the omitted one or more of the at least two targets into the candidate set during a second time interval outside the first time interval and during the treatment time and by determining whether the treatment plan can be determined for the candidate set and by determining the candidate set to be the set of targets if the treatment plan can be determined.

7. The method of claim 6, wherein the candidate set is determined by omitting one or more of the at least two targets during a time interval during which a potential treatment plan violates a volume reduction criterion, describing that, if projecting the at least two targets into a plane perpendicular to a spatially separate one of the one or more sub-beams and if projecting the cross sectional area of the spatially separate sub-beam into the plane, then there lies not more than one of the at least two projected spatially separate targets spatially separate, in particular by at least a predetermined distance, within the projected cross sectional area, in particular at least for not longer than a predetermined time, the potential treatment plan fulfilling the condition that all of the at least two targets are simultaneously treated all over the treatment time, the time interval being referred to as violation time interval, and by including the omitted one or more of the at least two targets into the candidate set during a time interval outside the violation time interval and inside the treatment time.

8. The method of claim 1, wherein the treatment plan is determined by combining sub-treatment plans which are to be performed one after the other during treatment time and which respectively describe treatment of a sub-set of the at least two targets, the sub-treatment plans being determined based on the spatial information on the targets of the respective sub-set, the treatment beam constraint data and the treatment beam criteria data, the sub-sets being selected so that each of the targets being included in at least one of the subsets and the sub-treatment plans fulfilling the volume reduction criterion, in particular the criterion a) describing that, if projecting the at least two targets into a plane perpendicular to a spatially separate one of the one or more sub-beams and if projecting the cross sectional area of the spatially separate sub-beam into the plane, then there lies not more than one of the at least two projected spatially separate targets spatially separate, in particular by at least a predetermined distance, within the projected cross sectional area, in particular at least for not longer than a predetermined time for all the targets of the sub-set.

9. The method of claim 8, wherein the treatment beam criteria data comprise that all targets of each subset are treated at least sequentially and preferably simultaneously in accordance with the respective sub-treatment plan during a sub-treatment time interval.

10. The method of claim 9, wherein the sub-sets are determined based on candidate sub-sets, and those one of the candidate sub-sets are selected as subset for which a sub-treatment plan can be determined which describes simultaneous treatment of all targets of the subset during the whole sub-treatment time while not violating the radiation reduction criterion.

11. The method of claim 1, wherein the candidate set is determined by omitting one or more of the at least two targets during a time interval during which a potential treatment plan violates the volume reduction criterion, in particular the criterion a) describing that, if projecting the at least two targets into a plane perpendicular to a spatially separate one of the one or more sub-beams and if projecting the cross sectional area of the spatially separate sub-beam into the plane, then there lies not more than one of the at least two projected spatially separate targets spatially separate, in particular by at least a predetermined distance, within the projected cross sectional area, in particular at least for not longer than a predetermined time, the potential treatment plan fulfilling the condition that all of the at least two targets are simultaneously treated all over the treatment time, the time interval being referred to as violation time interval, and by including the omitted one or more of the at least two targets into the candidate set during a time interval outside the violation time interval and inside the treatment time, wherein the treatment device comprises a beam source to issue the at least one treatment beam and wherein there is a path of movement of the beam source relative to the at least two targets referred to as treatment path, which is in particular a preferably arc-shaped relative movement of the beam source in at least one vertical plane relative to the at least two targets, the sub-treatment plans describing treatment during movement of the beam source along the treatment path and/or a section of the treatment path, a) wherein there is more than one complete movement of the beam source along the treatment path between a starting point and an end point and wherein the treatment of each of the subsets is respectively assigned to one of the complete movements so that by performing more than one complete movement all targets are treated, and in particular wherein the treatment plan is determined so that the treatment path is only changed by rotating the patient in a reference system in which the treatment device is at rest, in particular by rotating the plane, if and after all of the at least two targets have been treated, b) wherein targets omitted according to one of the sub-treatment plans during forward movement of the beam source along a first subsection of the treatment path are treated according to another sub-treatment plan during backward movement or during another forward movement along a second subsection of the treatment path which first subsection can be identical; and/or c) wherein targets omitted according to one of the sub-treatment plans during movement of the beam source along a first subsection of a first treatment path are treated according to another sub-treatment plan during movement along a second subsection of a second treatment path, wherein the first treatment path and the second treatment path are in particular different due to a movement of the patient in a reference system in which the treatment device is at rest, in particular by rotating the at least two targets relative to the vertical plane, wherein in particular the first and second subsection would be identical without the movement of the patient in the reference system.

12. The method according to claim 1, wherein the treatment plan which describes simultaneous treatment and which is used for the definition of the radiation reduction criterion is a treatment plan which has been determined by minimizing the healthy volume which is subjected to treatment radiation.

13. A computer program embodied on a non-transitory computer readable medium which, when running on a computer or when loaded onto a computer, causes the computer to
acquiring target data describing spatial information on the at least two spatially separate targets in a patient's body;
acquiring treatment beam constraint data which allow determination of potential treatment plans which can be realized by the treatment device and which potential treatment plans describe potential arrangements of the at least one treatment beam, referred to as potential treatment beam arrangements;
acquiring treatment beam criteria data describing criteria for the treatment of the at least two targets by the at least one treatment beam, the criteria comprising a radiation reduction criterion which describes that a treatment plan is allowed to be determined which describes a non-simultaneous treatment of the at least two targets at least for a time interval during the treatment time if this treatment plan describes that parts of the patient's body outside the at least two targets are less exposed to treatment radiation, in particular at least to a predetermined extent, compared to the case of a treatment plan which describes a simultaneous treatment of the at least two targets during the treatment time; and
determining the treatment plan which fulfils the radiation reduction criterion based on the target data, the treatment beam constraint data and the treatment beam criteria data.

14. A radiation therapy system, comprising:
a computer including the computer program of claim 13, wherein the computer program is executed on the computer or loaded onto the computer;
a couch for placing a patient;
and a treatment device comprising the beam shaping device and the beam source.

15. The radiation therapy system of claim 14, wherein the treatment device and the couch are movable relatively to each other, particularly wherein the couch is rotatable in a horizontal plane and/or the treatment device is movable along an arc-shaped pathway lying in a specifically vertically oriented plane.

* * * * *